United States Patent [19]

Corby

[11] Patent Number: 5,558,881
[45] Date of Patent: Sep. 24, 1996

[54] IODOPHORS, PRODUCTION AND USE THEREOF

[75] Inventor: Michael P. Corby, Ravenshead, England

[73] Assignee: Diversey Corporation, Mississauga, Canada

[21] Appl. No.: 217,197

[22] Filed: Mar. 24, 1994

[30] Foreign Application Priority Data

Mar. 26, 1993 [GB] United Kingdom .................. 93 06296

[51] Int. Cl.⁶ ........................................................ A01N 59/12
[52] U.S. Cl. ........................... 424/672; 424/669; 424/670; 424/671; 424/668
[58] Field of Search .................................. 424/672, 667, 424/668, 669, 670, 671; 252/106

[56] References Cited

U.S. PATENT DOCUMENTS

| | | | |
|---|---|---|---|
| 3,274,116 | 9/1966 | Mills | 252/106 |
| 4,113,857 | 9/1978 | Shetty | 424/150 |
| 4,258,056 | 3/1981 | Lentsch | 424/303 |
| 4,271,149 | 6/1981 | Winicov et al. | 424/150 |
| 4,288,428 | 9/1981 | Foll et al. | 424/78 |
| 4,376,787 | 3/1983 | Lentsch et al. | 424/315 |
| 4,822,513 | 4/1989 | Corby | 252/106 |
| 4,954,351 | 9/1990 | Sackler et al. | 424/667 |
| 4,996,048 | 2/1991 | Bhagwat et al. | 424/80 |
| 4,996,146 | 2/1991 | Kessler | 435/28 |
| 4,997,625 | 3/1991 | Simon et al. | 422/29 |
| 5,043,090 | 8/1991 | Camp et al. | 252/106 |
| 5,047,164 | 9/1991 | Corby | 252/106 |
| 5,126,127 | 6/1992 | Bhagwat et al. | 424/78.25 |
| 5,180,061 | 1/1993 | Khan et al. | 206/570 |
| 5,202,047 | 4/1993 | Corby | 252/106 |
| 5,232,914 | 8/1993 | Fellman | 514/23 |
| 5,261,353 | 11/1993 | Stevenson | 119/157 |
| 5,409,697 | 4/1995 | Gluck | 424/78.25 |

FOREIGN PATENT DOCUMENTS

| | | |
|---|---|---|
| 1334276 | 11/1977 | Australia . |
| 0528697A1 | 2/1993 | European Pat. Off. . |
| 0565288 | 10/1993 | European Pat. Off. . |
| 2000110 | 1/1990 | Japan . |
| 0293504 | 8/1928 | United Kingdom . |
| 1406540 | 9/1975 | United Kingdom . |
| 2066660 | 7/1981 | United Kingdom . |
| 2060385 | 6/1983 | United Kingdom . |
| 2066660 | 8/1984 | United Kingdom . |
| 2084875 | 4/1992 | United Kingdom . |
| WO8900006 | 1/1989 | WIPO . |

OTHER PUBLICATIONS

Skrabal, A., "Hypohalous Acids and Hypohalites. VII. The Temperature Coefficients of the Reciprocal Reactions of the Iodine–Iodate Equilibrium," *Chemical Abstracts*, vol. 9, No. 8, pp. 996–997 (1915) (Abstract).

Lievin, O., "Kinetic Study of Alkaline Solutions of Iodine," *Chemical Abstracts*, vol. 16, No. 8, pp. 3022–3023 (1922) (Abstract).

Skrabal, A., "The Calculation of Chemical Equilibrium from Measurements of Reaction Velocity," *Chemical Abstracts* vol. 6, No. 1, pp. 12–13, (1912) (Abstract).

WPI Abstract Accession No. 90–047901/07 and JP 0200000110A (Sanyo) (Abstract) (1993).

Block, S. S. "Disinfection, Sterilization and Preservation," Fourth Ed., pp. 152–166 (1991).

Chemical Abstracts, vol. 110, No. 9, Abstract No. 71113 and JP 63 225 308 (Abstracts) (1988).

Derwent WPI, AN 87–031774[05] and ES 8 608 317 (Abstract) (1988).

*Primary Examiner*—José G. Dees
*Assistant Examiner*—Deborah Lambkin
*Attorney, Agent, or Firm*—Harness, Dickey & Pierce, P.L.C.

[57] ABSTRACT

*Inter alia*, an iodophor preparation composition comprising, in addition to a carrier, an iodide source, an oxidant and an acid source, characterised in that at least one of the iodide source, the oxidant and the acid source is only available for reaction with the other components when dissolved in an aqueous medium at the point-of-use is disclosed.

9 Claims, No Drawings

IODOPHORS, PRODUCTION AND USE THEREOF

This invention relates to improved iodophors, production and use thereof; more particularly, it relates to iodophors prepared at the point-of-use, which are more stable, which are able to be more concentrated and which need contain less iodine for a given effect.

Iodine may be formed by reacting iodide and iodate under acidic conditions. Normally such a reaction would result in the precipitation of elemental iodine crystals. For example, EP-A-565288 shows that such a reaction, in the presence of a suitable carrier material, results in economically-useful iodophor products, without the need to utilise the current iodine complexing process; this complexing process being both costly and time-consuming. According to this teaching, in some instances the mixture of iodide and iodate is produced by dissolving elemental iodine in an alkaline medium, while in others pre-prepared salts of iodide and iodate are utilised, in molar or non-molar proportions, as the need arises.

There are several disadvantages associated with known iodophors. These are shared by the iodophors produced in accordance with the above teaching which, after all, is intended to produce "normal" products by less expensive means. The disadvantages may be expressed as follows:

(a) Iodine and organic materials tend to react slowly such that shelf-lives of products will be limited. A typical example of this would be a drop (of about one-fifth) in titratable iodine levels over a two year shelf-life. In order to counteract this tendency, the regulatory authorities insist on an overage inclusion, such that the product is of proven potency at the end of its stated shelf-life. Sometimes 20–30% of extra active iodine is incorporated to achieve this end and this is both wasteful of valuable resources and expensive.

(b) Iodine is hydrophobic and is only soluble in aqueous media using carrier materials to a limited degree. When producing a complex of iodine and surfactant, depending on the actual choice of surfactant, there is a level of iodine associated with that surfactant above which the complex becomes too hydrophobic and is therefore non-water-soluble. Above this level of iodine in a complex, hydrotropes or other surfactants are needed to solubilise the complex. As a general rule, somewhere between 10 and 20% w/w of iodine reacted with a carrier will cause the complex to be water-insoluble. Iodine itself has a rather aggressive nature to skin. The combination of the necessary level of iodine for full efficacy (normally 0.25–1.00% w/w), with the associated carrier surfactant (generally 5 to 10 times the level of iodine) results in a somewhat skin-aggressive system; therefore there is a need for considerable quantities of emollient materials in teat dip/spray formulations, for example, (such as 5–15% glycerol). Because of this need to include emollient systems in so-called teat dip/sprays for example, for use in the control of bovine mastitis, and because of the hydrophobicity of the complex, such products are not easily concentrated (although concentrates do exist at present for dilutions in the range of from 33 to 20% v/v). Packaging waste is becoming increasingly important from both a user and a legislative viewpoint, advances in concentration of such products are therefore desirable.

The iodine itself is implicated in both problems.

As indicated above, if iodide and iodate are reacted in acid medium, the following occurs:

$$5I^- + IO_3^- + 6H^+ \rightarrow 3I_2 + 3H_2O$$

Moreover, in the presence of a suitable carrier, substantially normal iodophor products result.

A consideration of the molar ratios gives the following:

$5I^{31} = 127 \times 5 = 635$ MW $IO_3^{31} = 127 + (3 \times 16) = 175$ MW $3I_2 = 127 \times 3 \times 2 = 762$ MW ∴ For each gram of iodine to form, there is required 0.833g of iodide and 0.229 g of iodate.

Conveniently, there are used potassium iodate and sodium iodide, or iodide generated from iodine.

Hence, for each gram of iodine, there is therefore needed 0.984 g of sodium iodide and 0.301 g of potassium iodate.

As illustrated in Example 9 of EP-A-565288, iodide salt and iodate salt may be employed to good effect. All of the original oxidative potential of the original iodine, when disassociated in alkaline medium, is vested in the iodate moiety. This moiety in percentage weight/weight terms comprises a very small part of the overall formulation. It is, therefore, possible to prepare a product which includes all the usual ingredients (e.g. carrier, emollients, buffers and iodide) and to add the relevant quantity of iodate at point-of-use as an activator. It is possible, of course, to withdraw as activator either the iodide or the acid from the mix for addition at point-of-use, but the iodate is the only oxidative, and therefore reactive, ingredient. It is therefore the preferred candidate for separation from the main formulation.

In one embodiment, the present invention provides an iodophor preparation composition comprising, in addition to a carrier, an iodide source, an oxidant and an acid source, characterised in that at least one of the iodide source, the oxidant and the acid source is only available for reaction with the other components when dissolved in an aqueous medium at the point-of-use.

At least one component of the present composition may be held separately from the other components until dissolution or the components may be together, but in a solid, non-reactive state. Generally, the oxidant which is capable of forming iodine from iodide under acid conditions is iodate. Preferably, the molar ratio of iodide:oxidant is sufficient for complete reaction, but an excess of oxidant may also be useful in some cases. Generally, the carrier is a surfactant, preferably a non-ionic surfactant, or a water-soluble polymer. The present compositions may also comprise at least one adjuvant, preferably selected from buffers, emollients, hydrotropes, viscesity and/or rheology modifying agents, and are commonly provided in the form of teat dips or sprays.

In another embodiment, the present invention provides a process for the production of an iodophor characterised in that it comprises dissolving such a composition in an aqueous medium at the point-of-use.

In a further embodiment, the present invention provides the use as a disinfectant of such an iodophor.

This surprising concept according to the present invention has the following advantageous consequences with particular reference to the preferred embodiment:

(a) Iodate, when isolated, will not degenerate and therefore when the product is prepared at point-of-use, no overages will be necessary. Indeed, increased shelf-lives of products may be expected.

(b) As the mix of ingredients without the iodate no longer contains hydrophobic iodine, the mix is totally hydrophilic and capable of greater than current concentration. By way of illustration, it is possible to pack all the necessary ingredients into a product for 10% v/v dilution. This will have implications for packaging and packaging waste, for example.

(c) Because all the oxidative power is vested in the iodate salt separated from the main body of the mix, and because the iodate salt is capable of regenerating iodide back to iodine, it may not be necessary to include in the main body of the mix the usual level of iodine as iodide; less may well suffice. When the mix is prepared at point-of-use, the iodate added or rendered reactive will regenerate iodide into iodine until its full oxidative capacity is exhausted. Therefore, it is possible to utilise a system which generates a lesser level of actual iodine present at any one time, but will behave as a full level of active ingredient due to regeneration of iodine from iodide:

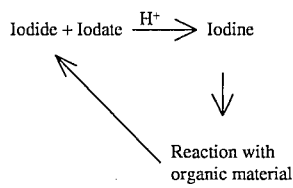

In this particular case the levels of actual iodine may be limited, while the total titratable material may be set at any level within reason by the percentage of iodate salt employed. The ability of this restrictive practice on the actual level of iodine generatable at any one time carries implications as to the actual levels of carrier needed for water-solubility and, as necessary, the levels of emollient needed to counteract the aggressive tendencies of the iodine and the carrier. Both the carrier and emollient levels may be reduced with consequent savings in valuable resources, while maintaining full efficacy.

Naturally, other suitable-oxidising agents may be used in place of iodate, for example monopersulphate or metaperiodate.

The following Examples are illustrative of the present invention:

EXAMPLE 1

| | % w/w | |
|---|---|---|
| Water | 84.36 | |
| Sodium iodide (anhydrous) | 0.49 | |
| Lutensol TO.12* | 4.00 | Part A used neat i.e. ready to use when activated |
| Sodium acetate | 0.50 | |
| Phosphoric acid (75%) | 0.40 | |
| Glycerine | 10.00 | |
| Potassium iodate | 0.15 Activator | |

(*Non-ionic surfactant obtainable from BASF; isotridecanol + 12 moles ethylene oxide)

NB: 0.49% w/w of sodium iodide is equivalent to 0.50% iodine after oxidation with iodate, a normal efficacious level. Usually up to 0.6% w/w iodine would be required.

In this Example all the ingredients in Part A are mixed until homogeneous and the activator is added at point-of-use. This illustration is of a ready-to-use product, i.e. no concentration of ingredients, but demonstrates the lack of overage requirements for the "drop in active during shelf-life" problem. The mixing of Part A and the activator results in a product containing 0.5% w/w iodine (a known efficacious level) and at a pH of about 3.5, i.e. physiologically-acceptable.

EXAMPLE 2

| | % w/w | |
|---|---|---|
| Water | 26.55 | |
| Sodium iodide | 2.46 | |
| Glycerine | 50.00 | Part A for use at 20% w/w in water |
| Lutensol TO.12 | 17.50 | |
| Phosphoric acid | 1.00 | |
| Sodium acetate | 2.00 | |
| Potassium iodate | 0.15% activator of final product weight | |

This Example illustrates the concentration ability of the present concept. At point-of-use, the product Part A is diluted 20% w/w into water and the activator is added or the activator and Part A are mixed and the whole diluted at 20% w/w into water. This results in a product containing 0.5% iodine at a pH of from about 3.5 to 4.0.

EXAMPLE 3

| | % w/w | |
|---|---|---|
| Water | 15.32 | |
| Sodium iodide | 0.98 | |
| Sodium acetate | 1.50 | Part A for use at 10% w/w in water |
| Phosphoric acid | 2.00 | |
| Glycerine | 70.00 | |
| Lutensol TO.12 | 10.00 | |
| Potassium iodate | 0.15% activator of final product weight | |

In this illustration, Part A is diluted 10% w/w at point-of-use and the activator again gives a level of 0.5% w/w iodine at a pH of 3.5–4.0. A typical volume used would be 25 litres ready-to-use made from 2.5 litres of Part A and 37.5 grams of activator being 0.15% w/w of 25 litres at S.G. 1.0.

Sodium iodide and "iodide" in general are expensive, while iodine is usually considerably cheaper. It is therefore possible to produce the iodide in Part A in situ:

EXAMPLE 4

| | % w/w | |
|---|---|---|
| Water | 25.0 | |
| Iodine | 0.83 | |
| Sodium metabisulphite | ~0.5 | Part A for use at 10% w/w |
| Sodium acetate | 1.5 | |
| Phosphoric acid (75%) | 2.0 | |
| Glycerine | 60.0 | |
| Lutensol TO.12 | 10.0 | |
| Potassium iodate | 0.15% activator of final product weight | |

This product is substantially identical to the previous Example, the only difference being that the iodine is dissolved first in the sodium metabisulphite solution. It is important not to exceed that exact quantity of metabisulphite needed to react with all the iodine. As indicated above, this embodiment of the present invention is cheaper than using iodide salt.

Other suitable activators include: sodium periodate $NaIO_4$ at 0.09% w/w of the final product weight and potassium monopersulphate $KHSO_5$ used at about 0.7% w/w of the final product weight. Such may be used in conjunction with any Part A mixture illustrated above.

Once the present products are prepared at point-of-use, the "normal" active degradation commences and a "use by" recommendation is needed. Typical use times for such products would be about one month per drum. It is therefore only necessary to include iodine to guarantee full potency after, say, 6 to 8 weeks, rather than the current two or three years for prepared product in the distribution chain.

Examples of prepared product stability are as follows:

EXAMPLE 5

| | |
|---|---|
| Water | QS |
| Iodine | 2.5 |
| Sodium metabisulphite | ~1.0 |
| Lutensol TO12 | 20.0 |
| Glycerine | 50.0 |
| Phosphoric acid (75%) | 1.5 |
| Sodium acetate | 2.5 |

Used at 20% w/w and activated using 0.15% w/w of final product weight of $KIO_3$.

(A small overage has been included in this formulation by dissolving 2.5% iodine, the exact amount would have been 2.08%. This is to give >0.5% $I_2$ on mixing and may well be reduced if the mixed product stability proves good.)

For the purposes of a stability study, the formulation of Example 5 "Part A" was held at 37° C. in glass, while the potassium iodate "Part B" was held in H.D. polythene at 50° C. It was estimated that the acceleration storage factor was about 3 times actual. Samples were assayed:

Iodine—using an N/10 sodium thiosulphate titration =$I_2$% w/w

Total iodine—as above, but with excess acid present =$I_{2T}$ % w/w pH in use—using buffered meter In a typical titration for $I_2$% w/w, the reaction slows as $I_2$% w/w approaches $I_{2T}$% w/w. In practical terms, $I_2$%/$I_{2T}$% will be about 90–92% complete when the reaction is practically completed, (i.e. 0.53% from 0.58 $I_{2T}$%). It was noted that the time to react about 90–92% completion got longer and longer as the study proceeded.

It was surmised that, with this formulation, the tendency towards longer and longer reaction times reflects less and less available acidity even though the actual initial pH does not seem to be rising (it was buffered). Keeping the acid and glycerol together was the probable cause.

The weight of activator obviously plays a large role in this reaction, so the activator was weighed very accurately and the titre vs activator weight is a true reflection of the stability of the overall product.

RESULTS

TABLE 1

| | To make 100 g of Ready-to-use Dip | | | | | |
|---|---|---|---|---|---|---|
| Days | Wt activator used g | $I_2$ % w/w | $I_{2T}$ % w/w | $I_{2T}$ act Wt ratio | Time to react mins. | pH initial |
| 0 | 0.153 | 0.53 | 0.56 | 3.66 | <5 | 3.9 |
| 20 | 0.151 | 0.53 | 0.57 | 3.77 | <5 | 3.8 |
| 30 | 0.152 | 0.52 | 0.58 | 3.81 | 10 | 3.8 |
| 57 | 0.148 | 0.51 | 0.53 | 3.58 | 20 | 3.9 |
| 94 | 0.148 | 0.50 | 0.54 | 3.65 | 20 | 3.9 |
| 131 | 0.154 | 0.52 | 0.57 | 3.70 | 30 | 3.9(5) |
| 210 | 0.154 | 0.53 | 0.58 | 3.77 | 30 | 3.9 |
| 270 | 0.148 | 0.51 | 0.56 | 3.78 | 30 | 3.8 |

This accelerated storage test indicates that even at 50° C., the activator (pure $KIO_3$) is not degraded in any way; there is no trend at all in the total iodine to activator weight ratio. While the titratable iodine figure obtainable without acid addition achieves 0.53 (or its equivalent dependent upon activator weight) the time taken to reach this level rises with age.

Part A and activator and water are mixed and the ready-to-use product is held at ambient:

| In-use solution Age weeks | Titrable iodine % w/w | pH |
|---|---|---|
| 0 | 0.53 | 3.8 |
| 1 | 0.52(5) | 4.3 |
| 3 | 0.53 | 4.2 |
| 8 | 0.52 | 4.4 |

Under these conditions of storage (35° C.), a typical known iodophor product degrades (as follows):

| Age Weeks | Iodine % w/w | pH |
|---|---|---|
| 0 | 0.56 | 4.5 |
| 1 | 0.53 | 3.8 |
| 2 | 0.51 | 3.2 |
| 4 | 0.50 | 3.1 |
| 8 | 0.50 | 3.0 |
| 20 | 0.49 | 3.0 |

EXAMPLE 6

| | % w/w | |
|---|---|---|
| PART A | | |
| Lutensol TO12 | 30.0 | for use |
| Glycerol | 50.0 | at 10–15% w/w |
| Water (deionised) | 20.0 | |
| PART B ACTIVATOR | | |
| Potassium iodate | 8.0 | for use at |
| Sodium acetate | 15.0 | 1.8% w/w to give |
| Sodium bisulphate | 51.0 | 0.5% iodine |
| Sodium iodide | 26.0 | |

In this formulation all the organics were in Part A, while all the required inorganics (possibly including acetate) are in the activator pack. This has the slight disadvantage of needing a larger activator pack volume.

Stability study held in laboratory at ambient. Made up to 50 ml of dip ready-to-use for titration.

TABLE 2

| Age | Wt Part A g | Wt Part B g | Iodine % w/w | pH |
|---|---|---|---|---|
| Initial | 5.01 | 0.90 | 0.52 | 3.2 |
| 2 days | 5.17 | 0.90 | 0.52 | 3.4 |
| 16 weeks | 5.00 | 0.90 | 0.52 | 3.2 |
| 24 weeks* | 5.00 | 0.90 | 0.49 | 3.3 |

*The storage container for Part B was found to be not properly sealed, moisture ingress had caused some caking of the powder and whilst the activity is still high, it has dropped a little. There is a tendency for a brown colour to develop in Part B, presumably as small amounts of moisture allow iodide and iodate to react (prematurely).

A number of illustrative formulations have been tried and it has been found that if the product is to be used on skin, there are two conflicting factors to be accommodated:

(a) sufficient acid is required to cycle the iodide/iodine/iodide system and this must be included in the product concentrate; while (b) the pH of the product to be used on cows' teats should not be below pH 3 when first made up.

It would appear that it is just about possible to achieve these two conflicting objectives. (i.e. 2500 ppm $I_2$ actual may be made to titrate as 5000 ppm $I_2$ with an initial pH of about 3.0).

A number of formulations were prepared, all to be activated with 0.15% w/w $KIO_3$ =5000$I_2$, but using iodide in Part A to achieve 5000 ppm, 2500 ppm and 1000 ppm iodine actually present.

A further set of samples was provided by preparing a direct equivalent based on a Lutensol TO12 iodine complex prepared in the conventional way and diluted to 5000, 2500 and 1000 ppm $I_2$.

The following formulations illustrate this iodine regeneration in use effect:

| Example | 7 | 8 | 9 |
|---|---|---|---|
| Water | QS | QS | QS |
| Iodine | 2.08 | 1.04 | 0.41 |
| Sodium bisulphite | ~1.10 | ~0.65 | ~0.22 |
| Lutensol TO12 | 20.00 | 10.00 | 4.00 |
| Glycerine | 40.00 | 20.00 | 8.00 |
| Sodium acetate | 2.00 | 2.00 | 2.00 |
| Phosphoric acid (75%) | 3.00 | 3.00 | 3.00 |

All for use at 20% w/w and all activated using 0.15% $KIO_3$.

| Example in use | 7 | 8 | 9 |
|---|---|---|---|
| Iodine actual level | 0.5 | 0.25 | 0.1 |
| Carrier level | 4.0 | 2.0 | 0.8 |
| Emollient level | 8.0 | 4.0 | 1.6 | for use at 20% w/w.

When activated using 0.15% $KIO_3$ all these formulations titrate as 0.50% w/w I2 with an initial pH of 2.9/3.0 in tap water. It will be noted that the required levels of carrier and emollient have been reduced in the ready-to-use product in order to accommodate the maximum of ~0.25% or 0.1% w/w $I_2$ to be generated at any one time.

While suspension testing is known to be insufficiently sensitive to differentiate between 5000, 2500 and 1000 ppm $I_2$ in use (all give no survivor results), it was hoped that an excised cows' teat surface disinfection test, the N.M.C. * Protocol A might differentiate. Results of these tests are provided in Table 3 below.

(* National Mastitis Council Inc.)

TABLE 3

Results of N.M.C. Protocol A

| | Material Tested | Log Reductions | |
|---|---|---|---|
| | | E. coli | S. aureus |
| | Complex 5000 $I_2$ | 3.56 | 2.58 |
| | Complex 2500 $I_2$ | 3.93 | 3.14 |
| | Complex 1000 $I_2$ | 3.52 | 2.53 |
| Example 7 | Regenerated 5000/5000 $I_2$ | 3.40 | 3.29 |
| Example 8 | Regenerated 2500/5000 $I_2$ | 3.21 | 2.96 |
| Example 9 | Regenerated 1000/5000 $I_2$ | 3.34 | 2.41 |

It was hoped that the N.M.C Protocol A test would differentiate between the standard levels of $I_2$ in the conventional products which it failed to do; at least, however, all the regenerated types were equivalent to the 5000 ppm complex standard. Although it may not be possible to demonstrate the regeneration effect microbiologically in vitro due to lack of test sensitivity, in vivo studies may be more successful. All of the regenerated products titrated chemically as 5000 ppm $I_2$.

The present approach of removing $IO_3-$, in particular, as activator gives good active stability. On the other hand, separating all of the inorganics as in Example 6 gives seemingly good stability, but a rather moisture-sensitive activator. Iodine regeneration would seem to offer efficiency with reduced resources. Keeping activators separate from the bulk of the formulation is viable and it gives 100% stability, removing the requirement for expensive overages, as well as allowing concentration of products not currently possible with "complex" technology. The concept of utilising less iodine (as iodide) and regenerating actual biocide allows the use of less of the expensive resources, such as carriers and emollients for equivalent efficacy.

If all ingredients are provided as dry powders, it is also possible to produce a single pack product. This may be achieved using sorbitol powder and a powder-form surfactant, such as Lutensol AT25 obtainable from BASF, for example.

| | % w/w |
|---|---|
| Potassium iodate | 1.22 |
| Sodium iodide | 3.82 |
| Sorbitol powder | 48.70 |
| Sodium hydrogen sulphate | 7.47 |
| Lutensol AT25* | 36.55 |
| Sodium acetate | 2.20 |

(*$C_{16}$–$C_{18}$ saturated alcohol with 25 moles of ethylene oxide condensed.)

For use at 13% w/w dissolved in water. As dissolved, this will result in 0.5% available iodine as an iodophor and ~6% of sorbitol in solution.

It is, of course, possible to use the iodine regeneration system in a powder product as illustrated in Example 11 below, whereby the levels of carrier and emollient may be reduced (or, more likely in practice, the use rate lowered).

| | % w/w |
|---|---|
| Potassium iodate | 2.20 |
| Sodium iodide | 3.44 |
| Sorbitol powder | 43.91 |

-continued

|  | % w/w |
|---|---|
| Sodium hydrogen sulphate | 13.47 |
| Lutensol AT25 | 33.00 |
| Sodium acetate | 3.97 |

For use at 7.2% w/w giving in the use solution approx. 0.25% w/w of iodine, but regeneratable as per 0.5% w/w with carrier at about 2.4% and emollient at about 3.2%.

Dry products might, for example, be provided as a range of water-soluble sachets for different levels with separate emollient as required.

I claim:

1. An iodophor preparation composition comprising, in addition to a carrier, an iodide source, an oxidant and an acid source, characterized in that the oxidant is reactive with the other components only when dissolved in an aqueous medium at the point-of-use, said oxidant being present in said composition in an excess amount sufficient for the complete generation of iodine from iodide in said composition.

2. A composition as claimed in claim 1 wherein at least one component is held separately from the other components until dissolution.

3. A composition as claimed in claim 1, wherein the components are together, in a solid, non-reactive state.

4. A composition as claimed in claim 1 wherein the oxidant is iodate.

5. A composition as claimed in claim 1, wherein the carrier is selected from a surfactant, a non-ionic surfactant, and a water-soluble polymer.

6. A composition as claimed in claim 1, wherein it also comprises at least one adjuvant selected from buffers, emollients, hydrotropes, viscosity and rheology modifying agents.

7. A composition as claimed in claim 1 wherein it is provided in the form of a teat dip or spray.

8. A process for the preparation of an iodophor characterized in that it comprises dissolving a composition as claimed in claim 1 in an aqueous medium at the point-of-use.

9. An iodophor composition produced by a process as claimed in claim 8, said composition being a disinfectant.

* * * * *